United States Patent
Wang et al.

(10) Patent No.: US 10,893,827 B2
(45) Date of Patent: Jan. 19, 2021

(54) DEVICE FOR MEASURING MUSCLE RELAXATION AND MONITORING EQUIPMENT

(71) Applicant: SHENZHEN MINDRAY BIO-MEDICAL ELECTRONICS CO., LTD., Shenzhen (CN)

(72) Inventors: Bin Wang, Shenzhen (CN); Jian Cen, Shenzhen (CN); Peng Zhang, Shenzhen (CN); Fang Liu, Shenzhen (CN); Hui Yu, Shenzhen (CN)

(73) Assignees: Shenzhen Mindray Bio-Medical Electronics Co., Ltd., Shenzhen (CN); Shenzhen Mindray Scientific Co., Ltd., Shenzhen (CN)

( * ) Notice: Subject to any disclaimer, the term of this patent is extended or adjusted under 35 U.S.C. 154(b) by 762 days.

(21) Appl. No.: 14/649,874

(22) PCT Filed: Sep. 9, 2013

(86) PCT No.: PCT/CN2013/083095
§ 371 (c)(1),
(2) Date: Oct. 1, 2015

(87) PCT Pub. No.: WO2014/086177
PCT Pub. Date: Jun. 12, 2014

(65) Prior Publication Data
US 2016/0183845 A1    Jun. 30, 2016

(30) Foreign Application Priority Data
Dec. 5, 2012 (CN) ............... 2012 1 0516742

(51) Int. Cl.
*A61B 5/11* (2006.01)
*A61B 5/00* (2006.01)
*A61B 5/22* (2006.01)

(52) U.S. Cl.
CPC ............... *A61B 5/11* (2013.01); *A61B 5/1114* (2013.01); *A61B 5/4519* (2013.01);
(Continued)

(58) Field of Classification Search
CPC .................. A61B 5/11; A61B 5/4519
See application file for complete search history.

(56) References Cited

U.S. PATENT DOCUMENTS 6,315,736 B1 * 11/2001 Tsutsumi ........... A61B 5/02405
600/500
8,187,209 B1 * 5/2012 Giuffrida ............. A61B 5/0488
600/595

(Continued)

FOREIGN PATENT DOCUMENTS

CN 201643223 U 11/2010
CN 102525490 A 7/2012
WO 2008031209 A1 3/2008

*Primary Examiner* — Daniel L Cerioni
*Assistant Examiner* — Raymond P Dulman
(74) *Attorney, Agent, or Firm* — Kory D. Christensen

(57) ABSTRACT

Disclosed are a device for measuring muscle relaxation and a monitoring equipment. The device includes a response signal detection unit and a control unit. The response signal detection unit includes an angular velocity sensor for sensing the motion of a measurement site and outputting corresponding angular velocity information of the measurement site to the control unit. The control unit includes a main processor and a stimulus signal source connected to the main processor. The stimulus signal source applies stimulus current to the measurement site through an output terminal under control of the main processor. The main processor can process the motion information from the response signal detection unit.

20 Claims, 2 Drawing Sheets

(52) U.S. Cl.
CPC ............ *A61B 5/6826* (2013.01); *A61B 5/742* (2013.01); *A61B 5/22* (2013.01); *A61B 5/72* (2013.01); *A61B 2562/0219* (2013.01)

(56) References Cited

U.S. PATENT DOCUMENTS

| | | | |
|---|---|---|---|
| 2004/0082979 A1* | 4/2004 | Tong .................... | A61N 1/0452 607/48 |
| 2006/0230108 A1* | 10/2006 | Tatsuta ................. | A61B 5/0002 709/204 |
| 2007/0027631 A1 | 2/2007 | Cabrera et al. | |
| 2007/0061106 A1* | 3/2007 | Vock ......................... | G01P 3/50 702/182 |
| 2011/0178760 A1* | 7/2011 | Schlumbohm ........ | A61B 5/1117 702/141 |
| 2013/0331711 A1* | 12/2013 | Mathur ................ | A61B 5/1106 600/483 |

* cited by examiner

DEVICE FOR MEASURING MUSCLE RELAXATION AND MONITORING EQUIPMENT

TECHNICAL FIELD

The present disclosure relates to medical devices, in particular to a device for measuring muscle relaxation and a monitoring equipment including the device.

BACKGROUND

In clinical settings, measurement of muscle relaxation can be used to detect the blocking level and recovery state of neuromuscular transfer function caused by relaxants given to anesthetized patients or critical patients. The conventional method for measuring muscle relaxation is to apply constant electrical current stimulus with a certain intensity and pulse width, according to different stimulus modes, to the corresponding nerve near the wrist of a patient, thus causing contractions of relevant muscles. The strength of a finger motion can reflect the depth of anesthesia of the patient.

The conventional device for measuring muscle relaxation usually utilizes an acceleration sensor to sense and output motion information of the body. For example, the acceleration sensor is attached to a measurement site, such as a thumb, and the motion of the acceleration sensor is regarded to be consistent with the motion of the thumb. Then the acceleration sensor outputs uniaxial acceleration information, biaxial acceleration information or triaxial acceleration information. The acceleration information then can be processed with algorithms to indicate the state of the body in response to the electrical current stimulus.

SUMMARY

The present disclosure provides a device for measuring muscle relaxation.

According to one aspect of the present disclosure, a device for measuring muscle relaxation is provided. The device may include a response signal detection unit and a control unit. The response signal detection unit can be used for detecting motion information of a measurement site in response to a stimulus current. The response signal detection unit includes an angular velocity sensor for detecting the angular velocity information of the measurement site and transmitting the angular velocity information to the control unit. The control unit includes a main processor and a stimulus signal source connected to the main processor. The stimulus signal source applies the stimulus current to the measurement site through an output terminal under control of the main processor. The main processor can be connected to the response signal detection unit by wired or wireless connection. The main processor can process the motion information from the response signal detection unit.

According to another aspect of the present disclosure, a monitoring equipment is provided. The monitoring equipment includes the device for measuring muscle relaxation. The monitoring equipment can display a measurement resulting from the motion information of the device for measuring muscle relaxation.

The device for measuring muscle relaxation according to the present disclosure utilizes an angular velocity sensor to detect the motion of the measurement site, and thereby can sense the angular velocity information to obtain the response information of the measurement site in response to the stimulus.

DETAILED DESCRIPTION

The present disclosure will be further described by the following detailed description of specific embodiments with reference to the accompanying drawings.

Figure 1:
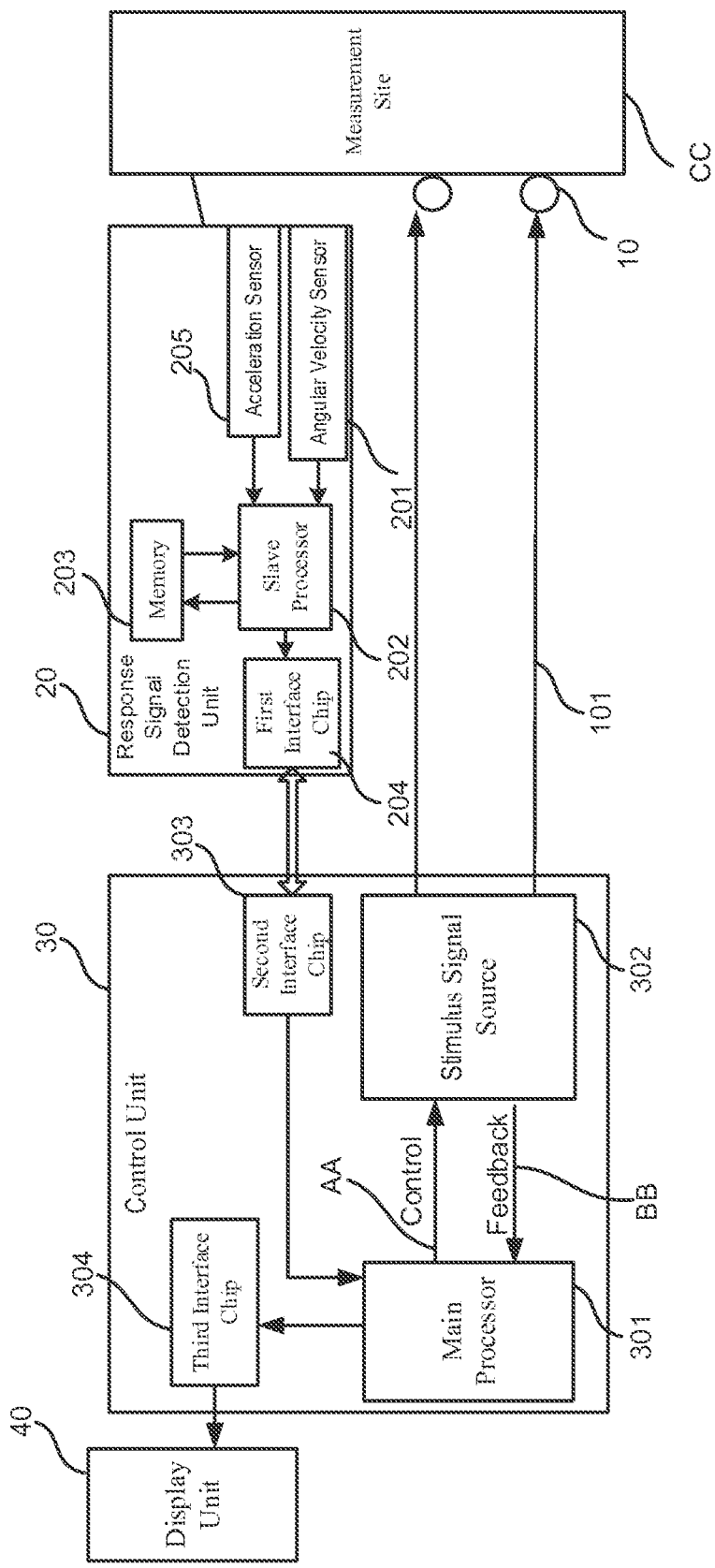
FIG. 1 is a block diagram of a device for measuring muscle relaxation according to one embodiment of the present disclosure.

Referring to FIG. 1, according to one embodiment, a device for measuring muscle relaxation includes a response signal detection unit 20, a control unit 30 and a display unit 40. The control unit 30 includes a main processor 301, a stimulus signal source 302, a second interface chip 303 and a third interface chip 304. The main processor 301 can be connected to the stimulus signal source 302. The second interface chip 303 and the third interface chip 304 can be connected to the main processor 301. The stimulus signal source 302 applies stimulus current to a measurement site CC through an output terminal 101 under control of the main processor 301. The measurement site CC can be a thumb. The output terminal 101 can be a pair of cables connected to the stimulus source 302, and one end of the output terminal 101 can be connected to an electrode pad 10 affixed to a surface of the measurement site CC. The electrode pad 10 can be affixed near the wrist. The stimulus signal source 302 can be controlled by the main processor 301 via a control interface AA. The stimulus signal source 302 generates stimulus current under control of the main processor 301, and applies the stimulus current to the measurement site CC via the output terminal 101 and the electrode pad 10. The output terminal 101 of the stimulus signal source 302 can also be connected to the main processor 301 so that the stimulus current can be fed back to the main processor 301; therefore the stimulus signal source 302 can be closed-loop controlled by the main processor 301. In one detailed embodiment, the stimulus current can be fed back to the main processor 301 via a feedback interface BB from the output terminal 101. The control of the stimulus signal source 302 under the main processor 301 is described with more detail as follows. In one aspect, the main processor 301 controls the stimulus signal source 302 to generate constant stimulation current required for the measurement of muscle relaxation. The intensity and/or the pulse width of the stimulus current are adjustable according to an acceptable body impedance range. In another aspect, in order to ensure the patient's safety, the main processor 301 monitors the stimulus current generated and fed back by the stimulus signal source 302, to determine whether the intensity and/or the pulse width of the stimulus current generated by the stimulus signal source 302 are kept within an allowable range according to the body impedance range. For the convenience of acquiring measurement results produced by the device for measuring muscle relaxation, the third interface chip 304, which can be regarded as one of the output terminals of the control unit 30, can be connected to the display unit 40. The main processor 301 acquires the motion information from the response signal detection unit 20, and processes the motion information to obtain processed data which can indicate the degree of the patient's muscle relaxation. The main processor 301 transmits the processed data via the third interface chip 304 to the display unit 40, by which the processed data is displayed accordingly. The second interface chip 303 can be connected to the response signal detection unit 20.

The response signal detection unit 20 includes an angular velocity sensor 201, a slave processor 202, a memory 203 and a first interface chip 204. The response signal detection unit 20 can be attached to the measurement site CC; thus the motion state of the response signal detection unit 20 can be regarded as consistent with the motion state of the measurement site CC. The angular velocity sensor 201 can be connected to the slave processor 202. The angular velocity sensor 201 detects and outputs angular velocity information of the measurement site CC when moving together therewith. The angular velocity information then can be transmitted to the slave processor 202. The slave processor 202 can also be used for parameter configuration or calibration of the angular velocity sensor 201. For example, the measuring range, filtering mode, and/or sampling rate of the angular velocity sensor 201 can be configured or set by the slave processor 202. The memory 203 can be connected to the slave processor 202. The memory 203 can be used for storing calibration information such as the zero offset of the angular velocity sensor 201, and thus can facilitate future hardware and software upgrades for the device. In another embodiment, the memory 203 can be used to store identity information such as hardware and/or software version information. The first interface chip 204, which can act as an output terminal of the response signal detection unit 20, is connected with the slave processor 202. The first interface chip 204 can be connected to the second interface chip 303. The motion information can be transmitted from the slave processor 202 to the main processor 301 via the first interface chip 204 and the second interface chip 303; thus the control unit 30 can obtain the motion information outputted by the response signal detection unit 20. The first interface chip 204 and the second interface chip 303 can be connected through conventional cabling or wireless connection, such as Bluetooth.

For further details, the response signal detection unit 20 and the control unit 30 can be set apart, but data can be transmitted between them through the first interface chip 204 and the second interface chip 303. In another embodiment, the response signal detection unit 20 and the control unit 30 can be integrated and attached to the measurement site CC together; therefore the processing of the motion information can be performed at the location of the measurement site CC, and the processed data or measurement results can be sent to the display unit 40 for displaying.

In another embodiment of the present disclosure, the slave processor 202 of the response signal detection unit 20 can be omitted. The memory 203 of the response signal detection unit 20 can be integrated with the control unit 30; thus the memory can be connected to the main processor 301 and used for storing the configuration or calibration information of the angular velocity sensor 201 and/or the identity information, such as the hardware and/or software version information of the device for measuring muscle relaxation.

In another aspect, the memory 203 can be an integrated part of the main processor 301 or the slave processor 202, or can be independent of or separated from the main processor 301 and the slave processor 202.

In order to obtain all necessary information for calculating the muscle relaxation measurements, the angular velocity information outputted by the angular velocity sensor 201 can be used to calculate approximate acceleration information according to certain assumptions. The assumptions can be described as follows: assuming that the measurement site (such as a thumb) performs a circular motion around a fixed point (such as the thumb joint), the angular velocity multiplied by the length of the measurement site can be a linear velocity, and a time derivative of the linear velocity speed can be regarded as the acceleration information. However, although the device of the present disclosure can get both the angular velocity and the acceleration through a single angular velocity sensor, it can further include an acceleration sensor to provide more accurate measuring of the muscle relaxation. In some embodiments, the response signal detection unit 20 includes an acceleration sensor 205. The acceleration sensor 205 can be connected to the slave processor 202. The acceleration sensor 205 detects and outputs acceleration information of the measurement site CC when moving together therewith. The acceleration information then can be transmitted to the slave processor 202. The slave processor 202 can also be used for parameter configuration or calibration of the acceleration sensor 205. The acceleration sensor 205 can be integrated in a single sensor chip with the angular velocity sensor 201. The acceleration sensor 205 and the angular velocity sensor 201 can also be separated from each other. In one embodiment, the angular velocity sensor 201 can be a gyroscope sensor. Other sensors, such as temperature sensors, magnetic sensors, and proximity sensors, can be employed in the device or incorporated with the angular velocity sensor 201 and/or the acceleration sensor 205 to measure other information of the measurement site CC.

Further, the slave processor 202 can be connected to the acceleration sensor 205, and the slave processor 202 can perform configuration or calibration of the acceleration sensor 205. The slave processor 202 can be connected to the main processor 301, such that the motion information sensed by the angular velocity sensor 201 and/or the acceleration sensor 205 can be transmitted from the slave processor 202 to the main processor 301, and therefore the propagation distance of the signal can be increased.

In one embodiment, the main processor 301 can process the acquired motion information according to the following principles or steps.

1. Assume the mass of the internal moving mass of the sensor of the response signal detection unit 20 is m, and m is an unchangeable constant. During the motion of the sensor, the internal moving mass is subject to two forces: one is the gravity represented by mg, and the other is the elasticity induced by the triaxial polysilicon spring of the sensor. The elasticity can be represented by f, and it can be regarded as the resistance against moving the internal mass. The resulting force of the gravity mg and the elasticity f can be represented by F, and therefore the actual acceleration of the internal moving mass, which is represented by A, is equal to F/m (A=F/m). Assume that $X_g$ represents a first vector of the gravity acceleration in the X-axis of the internal moving mass, $Y_g$ represents a second vector of the gravity acceleration in the Y-axis of the internal moving mass, and $Z_g$ represents a third vector of the gravity acceleration in the Z-axis of the internal moving mass. Similarly, $X_f$ represents a first vector of an elasticity acceleration in the X-axis, $Y_f$ represents a second vector of the elasticity acceleration in the Y-axis, and $Z_f$ represents a third vector of the elasticity acceleration in the Z-axis. $X_F$ represents a resulting force acceleration vector in the X-axis, $Y_F$ represents another vector of the resulting force acceleration in the Y-axis, and $Z_F$ represents another vector of the resulting force acceleration in the Z-axis. According to principles of the acceleration sensor, the acceleration sensor can output $X_f$, $Y_f$ and $Z_f$.

Figure 2:
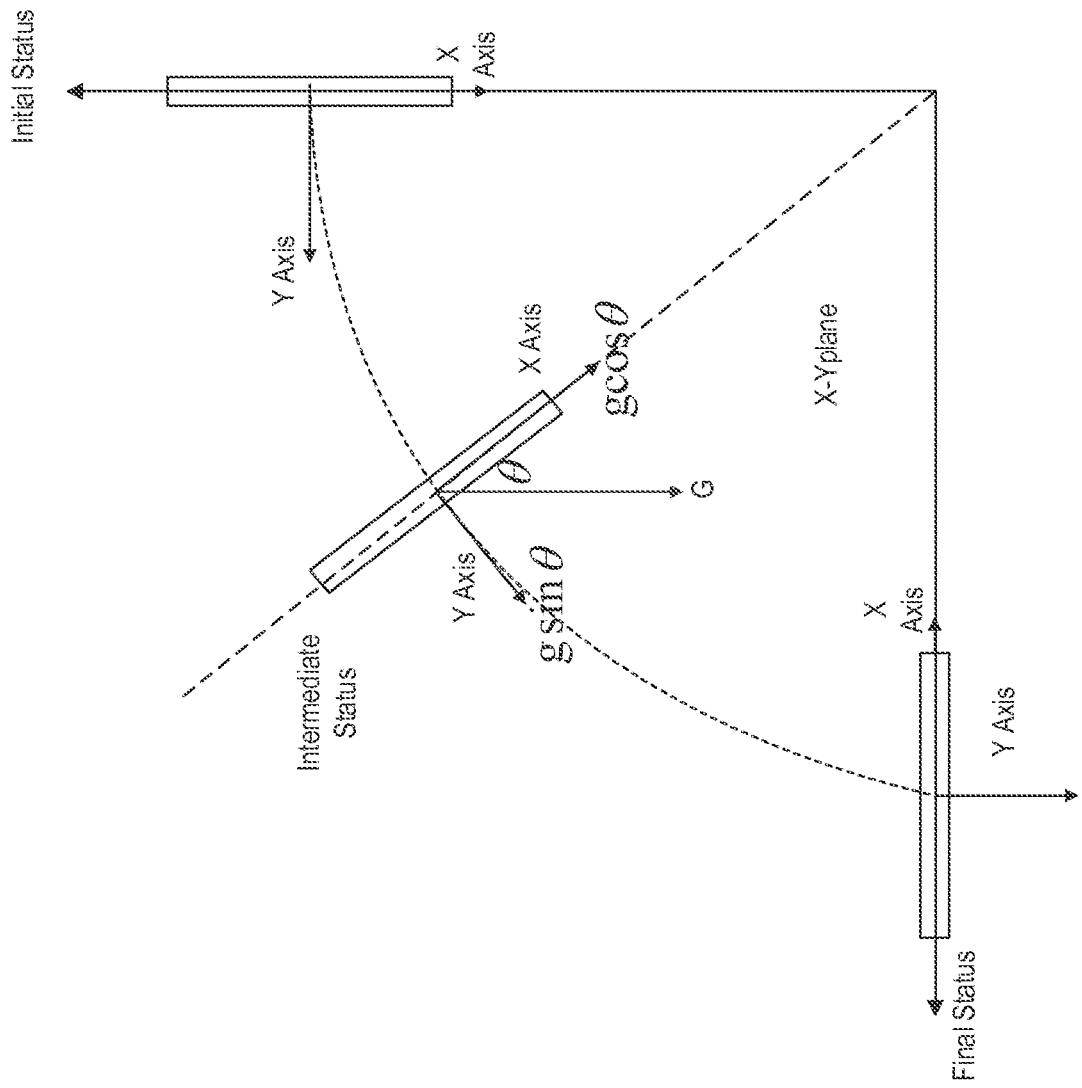
FIG. 2 is a schematic diagram depicting motions of a response signal detection unit in a two-dimensional plane.

Referring to FIG. 2, a schematic diagram depicts the motions of the response signal detection unit in a two-dimensional plane with a kinetic coordinate system. The two-dimensional plane can be represented by an X-Y plane which is parallel to the direction of the gravity. The internal mass of the sensor can be regarded as moving in the X-Y plane (assume there is no motion vector in the Z-axis). For any location or any moving status of the internal mass, equations including $X_F = g \cos\theta + X_f$, $Y_F = g \cos\varphi + Y_f$ and $Z_F = 0 + Z_f = 0$ are established, wherein $\theta$ is the angle between the gravity direction and the X-axis, and $\varphi$ is the angle between the gravity direction and the Y-axis. As the motions occur in the two dimensional plane, $\theta + \varphi = \pi/2$, and thus $Y_F = g \sin\theta + Y_f$. Therefore, the absolute value of A can be calculated according to expression of $|A| = \sqrt{X_F^2 + Y_F^2 + Z_F^2} = \sqrt{(g\cos\theta + X_f)^2 + (g\sin\theta + Y_f)^2}$, and the absolute value of F can be calculated according to the following expression ①:

$$|F| = m|A| = m\sqrt{(g\cos\theta + X_f)^2 + (g\sin\theta + Y_f)^2} \quad ①$$

2. The angle $\theta$ of the expression ① can be calculated by the acceleration sensor 205 and the angular velocity sensor 201 jointly. The initial angle $\theta_0$ corresponding to the initial status of the moving mass can be obtained according to angle detection mechanisms of the acceleration sensor. As the output of the angular velocity sensor is angular velocity, the angle variation $\Delta\theta$ can be obtained by integrating the angular velocity with respect to time. Therefore $\theta$ can be calculated by the expression of $\theta = \theta_0 + \Delta\theta$. Accordingly, the only unknown element of the expression ① for calculating |F| is m.

3. Taking a widely used TOF (Train of Four, which applies four clusters of stimuli to the measurement site) measuring mode as an example, the final result to be obtained is TOF, which is a ratio, and it can be calculated according to the expression $$TOF = \frac{\max|F_4|}{\max|F_1|},$$

wherein max |$F_1$| represents a maximum measurement of |$F_1$| according to the first stimulus, and max |$F_4$| represents a maximum measurement of |F| according to the fourth stimulus. As a result, the unknown element m is removed, and the TOF can be calculated.

4. In some actual measurements of muscle relaxation, the motion of the measurement site may be three-dimensional. For fully reflecting the motion or calculating the measurement in this situation, triaxial acceleration information and triaxial angular velocity information may be needed. According to the above consideration, the absolute value of F can be calculated according to the following expression:

$$|F| = m|A| = m\sqrt{(g\cos\theta + X_f)^2 + (g\cos\varphi + Y_f)^2 + (g\cos\delta + Z_f)^2}$$

wherein $\theta$ is the angle between the gravity direction and the X-axis vector of the moving mass, $\varphi$ is the angle between the gravity direction and the Y-axis vector of the moving mass, and $\delta$ is the angle between the gravity direction and the Z-axis vector of the moving mass. Thus the actual measurement result of the muscle relaxation can be calculated according to the above described principles.

In some other embodiments of the present disclosure, the main processor 301 of the device can implement the function of the slave processor 202; that is, the angular velocity sensor 201 can be configured or calibrated by the main processor 301 directly. In another embodiment, the response signal detection unit 20 and the control unit 30 can be integrated as a single unit and attached to the measurement site CC as a whole, and the motion information can be transmitted from the response signal detection unit 20 to the main processor 303 without the first interface chip 204 and the second interface chip 303. In addition, the function of the display unit 40 is to display information such that a user can obtain a visualized measurement output conveniently, so the display unit 40 should not be considered as a limitation to the scope of the present disclosure.

The embodiments of the present disclosure provide a muscle relaxation measuring device including an angular velocity sensor to detect motion information of the measurement site, thereby obtaining the reaction of the measurement site under the current stimulus. In some of the embodiments, an acceleration sensor can be combined to obtain acceleration information of the measurement site directly, and thus the measuring of the muscle relaxation may be more accurate.

The present disclosure also provides a patient monitoring equipment which includes the above described muscle relaxation measuring device according to various embodiments. The patient monitoring equipment can display the measurement results of the muscle relaxation measuring device.

Though the present disclosure has been described in detail by way of specified examples, the examples are used for helping to understand the present disclosure, not to limit the present disclosure. Those skilled in the art can change the above specified embodiments based on the spirit of the present disclosure.

What is claimed is:

1. A device for measuring muscle relaxation, comprising:
an angular velocity sensor that senses a motion of a measurement site in response to a stimulus current and outputs corresponding angular velocity information of the measurement site to a control unit; and
an acceleration sensor that senses acceleration information of the measurement site and outputs the acceleration information to the control unit;
wherein the control unit is connected to the angular velocity sensor and the acceleration sensor, and wherein the control unit comprises:
a main processor that:
generates instructions for a stimulus signal source to generate the stimulus current that will be applied to the measurement site,
receives feedback of the stimulus current being generated by the stimulus signal source,
generates instructions for the stimulus signal source to modify intensity and/or pulse width of the stimulus current being applied to the measurement site so that the modified stimulus current falls within a pre-defined range according to a specific body impedance range based on the received feedback, and
processes the angular velocity information from the angular velocity sensor and the acceleration information from the acceleration sensor to determine a measurement result of muscle relaxation,
wherein the stimulus signal source is configured to apply the stimulus current to the measurement site based on the generated instructions from the main processor through an output terminal, and
wherein the main processor is further configured to:

acquire the acceleration information output by the acceleration sensor, wherein the acceleration information includes components, in an X-axis of an X-Y plane parallel to a direction of gravity, of an acceleration generated by a resistance that resists movement of a moving mass of the acceleration sensor;

acquire an initial angle between a gravity direction corresponding to an initial status of the moving mass and the X-axis;

acquire the angular velocity information output by the angular velocity sensor and calculate an angle variation during moving based on the angular velocity information;

calculate a resultant acceleration of the moving mass based on the initial angle, the angle variation, a gravity acceleration, and the acceleration information; and calculate the measurement result of muscle relaxation based on the resultant acceleration.

2. The device for measuring muscle relaxation according to claim 1, further comprising a display unit that displays a measurement result resulting from the motion information, wherein the display unit is connected to the control unit.

3. The device for measuring muscle relaxation according to claim 1, further comprising a slave processor that configures and/or calibrates the angular velocity sensor and/or transmits the motion information to the main processor, wherein the slave processor is connected to the angular velocity sensor.

4. The device for measuring muscle relaxation according to claim 1, further comprising a response signal detection unit that comprises a slave processor that configures and/or calibrates the angular velocity sensor and/or the acceleration sensor, and/or transmits the motion information to the main processor, wherein the slave processor is connected to the angular velocity sensor and the acceleration sensor respectively.

5. The device for measuring muscle relaxation according to claim 3, further comprising a memory that stores at least one of configuration information, calibration information and identity information of software versions and/or hardware versions of the device for measuring muscle relaxation, wherein the memory is connected to the slave processor or the main processor.

6. The device for measuring muscle relaxation according to claim 3, further comprising a first interface chip connected to the slave processor, and a second interface chip connected to the main processor, wherein the first interface chip and the second interface chip transmit the motion information from the slave processor to the main processor by wired or wireless connection.

7. The device for measuring muscle relaxation according to claim 1, wherein the stimulus signal source is connected to the main processor and feeds back the stimulus current to the main processor.

8. A monitoring equipment, comprising:
an angular velocity sensor that senses a motion of a measurement site in response to a stimulus current and outputs corresponding angular velocity information of the measurement site to a control unit; and
an acceleration sensor that senses acceleration information of the measurement site and outputs the acceleration information to the control unit;
wherein the control unit is connected to the angular velocity sensor and the acceleration sensor, and wherein the control unit comprises:

a main processor that:
generates instructions for a stimulus signal source to generate the stimulus current that will be applied to the measurement site,
receives feedback of the stimulus current being generated by the stimulus signal source,
generates instructions for the stimulus signal source to modify intensity and/or pulse width of the stimulus current being applied to the measurement site so that the modified stimulus current falls within a pre-defined range according to a specific body impedance range based on the received feedback, and
processes the angular velocity information from the angular velocity sensor and the acceleration information from the acceleration sensor to determine a measurement result of muscle relaxation,
wherein, the stimulus signal source is configured to apply the stimulus current to the measurement site based on the generated instructions from the main processor through an output terminal, and
wherein the main processor is further configured to:
acquire the acceleration information output by the acceleration sensor, wherein the acceleration information includes components, in an X-axis of an X-Y plane parallel to a direction of gravity, of an acceleration generated by a resistance that resists movement of a moving mass of the acceleration sensor;
acquire an initial angle between a gravity direction corresponding to an initial status of the moving mass and the X-axis;
acquire the angular velocity information output by the angular velocity sensor and calculate an angle variation during moving based on the angular velocity information;
calculate a resultant acceleration of the moving mass based on the initial angle, the angle variation, a gravity acceleration, and the acceleration information; and
calculate the measurement result of muscle relaxation based on the resultant acceleration.

9. The monitoring equipment according to claim 8, further comprising a display unit that displays the measurement result.

10. A method for measuring muscle relaxation, comprising:
applying a stimulus current to a measurement site via a stimulus signal source based on generated instructions from a main processor through an output terminal;
receiving, at a control unit, a feedback of the stimulus current being generated by the stimulus signal source;
modifying, via the control unit, an intensity and/or pulse width of the stimulus current being generated applied to the measurement site so that the modified stimulus current falls within a pre-defined range according to a specific body impedance range based on the received feedback;
sensing, via an angular velocity sensor, motion of the measurement site based on the applied stimulus current;
outputting, via a response signal detection unit, corresponding angular velocity information of the measurement site based on the sensed motion and acceleration information;
processing, via the control unit, the angular velocity information and the acceleration information to obtain a measurement result, wherein the measurement result corresponds to a degree of muscle relaxation; and displaying the measurement result on a display unit, wherein processing, via the control unit, the angular velocity information and the acceleration information to obtain the measurement result comprises:

acquiring the acceleration information output by the acceleration sensor, wherein the acceleration information includes components, in an X-axis of an X-Y plane parallel to a direction of gravity, of an acceleration generated by a resistance that resists movement of a moving mass of the acceleration sensor;

acquiring an initial angle between a gravity direction corresponding to an initial status of the moving mass and the X-axis;

acquiring the angular velocity information output by the angular velocity sensor and calculating an angle variation during moving based on the angular velocity information;

calculating a resultant acceleration of the moving mass based on the initial angle, the angle variation, a gravity acceleration, and the acceleration information; and calculating the measurement result of muscle relaxation based on the resultant acceleration.

11. The method for measuring muscle relaxation according to claim 10, further comprising configuring and/or calibrating the angular velocity sensor.

12. The method for measuring muscle relaxation according to claim 10, further comprising transmitting the angular velocity information.

13. The method for measuring muscle relaxation according to claim 10, further comprising storing at least one of configuration information, calibration information and identity information of software versions and/or hardware versions of a device for measuring muscle relaxation.

14. The method for measuring muscle relaxation according to claim 10, further comprising feeding back the stimulus current.

15. The device for measuring muscle relaxation according to claim 1, wherein the resultant acceleration is calculated according to a formula of:

$$|A|=\sqrt{(g\cos\theta+X_f)^2+(g\sin\theta+Y_f)^2}$$

where A is the resultant acceleration, $X_f$ and $Y_f$ represent the components, in the X-axis of the X-Y plane and a Y-axis of the X-Y plane, of the acceleration generated by the resistance that resists the movement of the moving mass respectively, g is the gravity acceleration, and θ is the angle between the gravity direction during moving and X-axis.

16. The device for measuring muscle relaxation according to claim 1, wherein the measurement result of muscle relaxation is calculated according to a formula of:

$$TOF = \frac{\max|F_4|}{\max|F_1|}$$

where TOF represents the measurement result of muscle relaxation, $\max|F_1|$ and $\max|F_4|$ represent maximum values of resultant forces produced by first and fourth measurements in a complete muscle relaxation measurement, respectively, and each resultant force is equal to a product of a resultant acceleration corresponding to the resultant force and a mass of the moving mass, wherein the resultant force is calculated according to a formula of:

$$|F|=m|A|=m\sqrt{(g\cos\theta+X_f)^2+(g\sin\theta+Y_f)^2}$$

where m represents the mass of the moving mass.

17. The monitoring equipment according to claim 8, wherein the resultant acceleration is calculated according to a formula of:

$$|A|=\sqrt{(g\cos\theta+X_f)^2+(g\sin\theta+Y_f)^2}$$

where A is the resultant acceleration, $X_f$ and $Y_f$ represent the components, in the X-axis of the X-Y plane and a Y-axis of the X-Y plane, of the acceleration generated by the resistance that resists the movement of the moving mass respectively, g is the gravity acceleration, and θ θ is the angle between the gravity direction during moving and X-axis.

18. The monitoring equipment according to claim 8, wherein the measurement result of muscle relaxation is calculated according to a formula of:

$$TOF = \frac{\max|F_4|}{\max|F_1|}$$

where TOF represents the measurement result of muscle relaxation, $\max|F_1|$ and $\max|F_4|$ represent maximum values of resultant forces produced by first and fourth measurements in a complete muscle relaxation measurement, respectively, and each resultant force is equal to a product of a resultant acceleration corresponding to the resultant force and a mass of the moving mass, wherein the resultant force is calculated according to a formula of:

$$|F|=m|A|=m\sqrt{(g\cos\theta+X_f)^2+(g\sin\theta+Y_f)^2}$$

where m represents the mass of the moving mass.

19. The method for measuring muscle relaxation according to claim 10, wherein the resultant acceleration is calculated according to a formula of:

$$|A|=\sqrt{(g\cos\theta+X_f)^2+(g\sin\theta+Y_f)^2}$$

where A is the resultant acceleration, $X_f$ and $Y_f$ represent the components, in the X-axis of the X-Y plane and a Y-axis of the X-Y plane, of the acceleration generated by the resistance that resists the movement of the moving mass respectively, g is the gravity acceleration, and θ θ is the angle between the gravity direction during moving and X-axis.

20. The method for measuring muscle relaxation according to claim 10, wherein the measurement result of muscle relaxation is calculated according to a formula of:

$$TOF = \frac{\max|F_4|}{\max|F_1|}$$

where TOF represents the measurement result of muscle relaxation, $\max|F_1|$ and $\max|F_4|$ represent maximum values of resultant forces produced by first and fourth measurements in a complete muscle relaxation measurement, respectively, and each resultant force is equal to a product of a resultant acceleration corresponding to the resultant force and a mass of the moving mass, and wherein the resultant force is calculated according to a formula of:

$$|F|=m|A|=m\sqrt{(g\cos\theta+X_f)^2+(g\sin\theta+Y_f)^2}$$

where m represents the mass of the moving mass.

* * * * *